(12) United States Patent
Kulik et al.

(10) Patent No.: US 12,036,705 B2
(45) Date of Patent: Jul. 16, 2024

(54) DEVICE AND METHOD FOR PRODUCING MICROSTRUCTURES

(71) Applicant: LTS Lohmann Therapie-Systeme AG, Andernach (DE)

(72) Inventors: Michael Kulik, Urmitz (DE); Nikolaj Tissin, Eschweiler (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 84 days.

(21) Appl. No.: 17/636,996

(22) PCT Filed: Aug. 18, 2020

(86) PCT No.: PCT/EP2020/073039
§ 371 (c)(1),
(2) Date: Feb. 21, 2022

(87) PCT Pub. No.: WO2021/032701
PCT Pub. Date: Feb. 25, 2021

(65) Prior Publication Data
US 2022/0362973 A1   Nov. 17, 2022

(30) Foreign Application Priority Data
Aug. 22, 2019   (DE) .................... 10 2019 122 648.1

(51) Int. Cl.
  *B29C 43/36*   (2006.01)
  *B29C 43/02*   (2006.01)
  *B29L 31/00*   (2006.01)

(52) U.S. Cl.
  CPC .......... *B29C 43/361* (2013.01); *B29C 43/021* (2013.01); *B29L 2031/7544* (2013.01); *B29L 2031/756* (2013.01)

(58) Field of Classification Search
  None
  See application file for complete search history.

(56) References Cited

U.S. PATENT DOCUMENTS

| 2002/0082543 A1 | 6/2002 | Park et al. |
| 2008/0088066 A1 | 4/2008 | Ferguson et al. |
| 2008/0275400 A1 | 11/2008 | Ferguson |
| 2009/0234301 A1 | 9/2009 | Tomono |
| 2011/0152792 A1 | 6/2011 | Takada |
| 2013/0144217 A1 | 6/2013 | Ross |

FOREIGN PATENT DOCUMENTS

| CA | 3174016 A1 * | 10/2021 | ........ A61M 37/0015 |
| EP | 2090331 A1 | 8/2009 | |
| KR | 101697556 B1 | 1/2017 | |
| WO | 2006062974 A2 | 6/2006 | |
| WO | 2008062832 A1 | 5/2008 | |
| WO | 2015174160 A1 | 11/2015 | |

* cited by examiner

Primary Examiner — Robert J Grun
(74) Attorney, Agent, or Firm — The Webb Law Firm

(57) ABSTRACT

A device for producing microstructures, particularly microneedles and more particularly microneedle arrays, including a female mold that has, on a top side, at least one in particular conical depressed portion for producing a microstructure. The female mold is, for example, in the form of a silicone cap and is connected to a hollow cylinder, in particular via a holding element. A plunger is disposed movably inside the hollow cylinder.

15 Claims, 2 Drawing Sheets

DEVICE AND METHOD FOR PRODUCING MICROSTRUCTURES

CROSS-REFERENCE TO RELATED APPLICATIONS

This application is the United States national phase of International Application No. PCT/EP2020/073039 filed Aug. 18, 2020, and claims priority to German Patent Application No. 10 2019 122 648.1 filed Aug. 22, 2019, the disclosures of which are hereby incorporated by reference in their entirety.

BACKGROUND OF THE DISCLOSURE

The disclosure relates to a device as well as to a method for manufacturing microstructures, in particular microneedles.

DESCRIPTION OF RELATED ART

The microneedles to be manufactured are preferably microneedles which are in particular arranged in a microneedle array. Microneedles are used to deliver active ingredients directly into the skin, which is also referred to as transdermal delivery. For this purpose, the microneedles have a length just sufficient to penetrate only into the outer skin layers, but preferably not to reach nerves and blood vessels and to thereby leave these unharmed. Nevertheless, microneedles create small holes in the upper skin layers, whereby the absorption of active ingredients is significantly increased when compared with a purely external application of active ingredients on the skin.

Microneedle arrays comprising a plurality of microneedles which is for example attached to a carrier surface, may be used for short-term delivery or for long-term application. A preferred possibility for delivering the active ingredient from the microneedles into the skin is that portions of the microneedles that contain active ingredients or the entire microneedle become dissolved or detached and are thus absorbed by the body via the skin. To this end, the microneedles are made, at least in part, in particular of water-soluble ingredients or materials. In addition to the direct delivery of active ingredients through the microneedles themselves, it is also possible for the microneedles to have pores or cavities or to be formed as hollow needles in order to allow such a delivery of active ingredients into the skin. In addition, microneedles may per se also be free of active ingredients. In this case, for example, the active ingredient may be applied externally to the outside of the microneedles, or a substance containing active ingredients can be applied to the corresponding skin area only after the microneedles have been removed from the skin, in order to thereby deliver active ingredients by using microneedles.

Microneedles may be made of ceramic, metal or polymer. It is preferred that one or more active ingredient components are added to these materials and a formulation of the microneedles is thus obtained.

Previously known methods for the production of therapeutic or diagnostic microneedles or microneedle arrays are not suitable, or only to a limited extent, for a production with sufficient quality and/or in sufficient numbers.

A common method for producing microneedles consists of casting the microneedles or entire microneedle arrays, using, for example, a mold made of silicone. In particular, due to the hydrophobic properties between the mold and the mostly liquid formulation applied thereon, various problems arise with such production processes.

In particular, there is the problem that the tolerances to be observed for the microneedles are extremely small. On the one hand, correspondingly small tolerances have to be ensured for the female molds, i.e. in particular the silicone molds, and on the other hand, the production processes must also be performed with correspondingly small tolerances.

The production of microneedles requires an aseptic processing, since the active ingredient has to be processed openly in the production environment. With numerous active ingredients, a posterior sterilization is not possible. This results in the demand for an aseptic production in which sterile disposable products are used. By using sterile disposable products, the risk of contaminations is avoided.

SUMMARY OF THE DISCLOSURE

It is an object of the disclosure to provide a device and a method for producing microstructures, in particular microneedles, with which microstructures can be produced with very small tolerances.

According to the disclosure, the object is achieved by a device according to claim 1 and a method according to claim 11, respectively.

The device of the present disclosure serves in particular for the production of in particular dissolving microstructures such as microneedles and, as is particularly preferred, for the production of microneedle arrays. The device comprises a female mold having at least one, preferably conical depression on an upper side. The depression serves to produce the microstructure, in particular by a casting method, that is, by applying a mostly liquid formulation onto the upper side of the female mold in particular in a dosed manner and distributing the same, and by curing the formulation to produce the microstructure.

Further, the device comprises a hollow cylinder. The same is preferably part of a basic element or forms a basic element. According to the disclosure, the female mold comprises a holding element or is connected to a holding element so that the female mold can be fastened or retained on the hollow cylinder. The female mold spans or covers an opening of the hollow cylinder. In particular, the female mold rests on the edge of the opening of the hollow cylinder in an initial state or a rest state before the female mold is used or filled with a formulation. The hollow cylinder is in particular a cylinder with a circular cross section.

A plunger is arranged in the hollow cylinder. The same is displaceable in the longitudinal direction of the hollow cylinder. In particular, the plunger may be inserted into the hollow cylinder starting from an initial or rest position to an inserted or upper position so that an upper side of the plunger rests on a lower side of the female mold, wherein the lower side of the female mold is directed towards the interior of the hollow cylinder. Here, it is particularly preferred that the plunger is inserted into the hollow cylinder to such an extent that the female edge is no longer in contact with the edge of the opening of the hollow cylinder, but is lifted off the same. In this manner, small tolerances can be achieved. Regardless of whether the female mold rests on the opening of the hollow cylinder in the initial or rest position, the disclosure has the essential advantage that by inserting the plunger into the hollow cylinder such that the female mold only rests on the upper side of the plunger, the possibly adding tolerances can be reduced. In the inserted or upper position, only the tolerance of the thickness of the female mold is still relevant. Tolerances which would be caused by the hollow cylinder are excluded thereby. This allows for a lower tolerance quality of the hollow cylinders as well as of their holding element, since the process tolerance is established via the plungers. Thus, by lifting the female mold, the tolerance chain is broken and the tolerance is reduced to the thickness of the female mold.

In a particularly preferred embodiment, the holding element connected to the female mold comprises an elongatable, in particular elastic intermediate element. Thereby, it is possible to lift the female mold off the edge of the hollow cylinder opening in a simple manner when inserting the plunger. When the plunger is withdrawn, the intermediate element automatically shortens again so that the female mold once more rests on the edge of the opening of the hollow cylinder. In this position, the formulation introduced into the cavity of the female mold can be cured.

Furthermore, it is preferred that the holding element comprises a connecting element for connection to the hollow cylinder. Here, the connection may be frictional, while a positive connection is preferred.

For this purpose, the connecting element is preferably designed as a latching element. As a connecting element, the holding element comprises, for example, tabs that engage into recesses provided in the hollow cylinder. Likewise, the hollow cylinder may have tabs that engage into corresponding recesses of the holding element. This makes it possible to arrange the female mold on the hollow cylinder in a precise position. In a particularly preferred embodiment, female molds connected to the hollow cylinders are used as sterile units or delivered to the production site as a sterile unit. After the production of the microstructure, this unit is preferably disposed of without the plunger or, if applicable, sterilized prior to being used again.

In a particularly preferred embodiment, the intermediate element is connected to the connecting element and the female mold. It is particularly preferred that the female mold and the intermediate element, and in particular the female mold of the intermediate element and the connecting element, are formed integrally. Silicone is particularly suitable as a material. It is particularly preferred that the holding element surrounds the hollow cylinder preferably in the circumferential direction, in particular completely. In particular in the case of an integral design of the female mold with the holding element, possibly together with the intermediate element and the connecting element, the same is cap-shaped and may, for example, be slipped over the hollow cylinder or be inserted into the hollow cylinder.

In a particularly preferred embodiment, the holding element surrounds the hollow cylinder on its outer side in the circumferential direction, in particular completely, or rests on an inner side of the hollow cylinder, preferably completely in the circumferential direction, In a particularly preferred embodiment of the disclosure, a plurality of hollow cylinders is provided, for example, connected to a common base element. Here, the hollow cylinders arranged in particular in columns and rows and are produced, for example, integrally as a plastic injection molded element. A female mold is connected to each individual hollow cylinder, which mold, as explained above, may be designed in particular as a silicone cap which is slipped over a hollow cylinder and/or inserted into a hollow cylinder. Furthermore, it is preferred that a plurality of plungers is provided which are also connected to each other, in particular as a group, and are displaced together.

Here, the number of plungers may correspond to the number of hollow cylinders so that when all the plungers are inserted into the hollow cylinders all female molds rest on the upper side of the plungers and are, in particular, lifted off the edge of the individual hollow cylinders. The group of plungers may, however, have a smaller number than the number of the hollow cylinders, so that microneedles are always produced in groups. For example, a group of four plungers may be inserted into the hollow cylinders, so that the female molds can rest correspondingly on the upper side of the plunger and are, in particular, lifted off the edge of the hollow cylinder. Subsequently, the cavities in the female molds are filled with a formulation applied in particular by means of nozzles. In the next step, the plungers are retracted, so that the female molds rest on the edges of the hollow cylinders again. Thereafter, the group of plungers and/or the group of hollow cylinders are displaced, so that the plungers are arranged below another group of female molds and the corresponding process can be repeated.

The disclosure further relates to a method for producing microstructures, in particular microneedles and more preferably microneedle arrays. The method is preferably executed using the above described device.

In a first step, the at least one plunger is inserted into the respective associated hollow cylinder, so that an upper side of the plunger rests on a lower side of the female mold. Finally, the at least one cavity of the female mold is filled with a formulation. Suitable formulations are, in particular, PVP, PLGA, polymer, sugar. Thereafter, the at least one plunger is retracted and, in particular after curing, the microstructure is removed from the female mold.

The at least one plunger is preferably inserted into the hollow cylinder such that the female mold is lifted off the edge surrounding the opening of the hollow cylinder in order to obtain the achievable tolerances.

Preferably, when the at least one plunger is retracted, the intermediate element of the holding element, which is connected to the female mold and is formed in particular in one piece, shortens such that the lower side of the female mold again rests on the edge surrounding the opening of the hollow cylinder. In this position, the formulation introduced into the at least one cavity can be cured.

It is preferred that a plurality of female molds are provided which are filled individually one after the other or in groups, with the method of the present disclosure being advantageously developed as described above with reference to the device.

The disclosure will be explained in more detail hereinafter with reference to a preferred embodiment and to the accompanying drawings.

DETAILED DESCRIPTION

Figure 1:
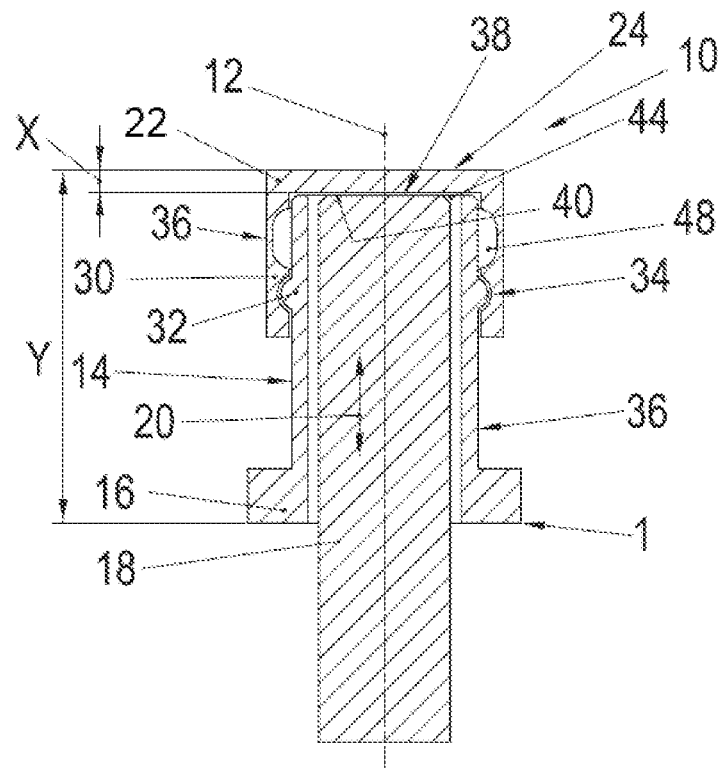
FIG. 1 shows a schematic sectional view of a first preferred embodiment of the device.

The first preferred embodiment of the disclosure schematically illustrated in FIG. 1 comprises a cap 10 made in particular of a silicon material, which is formed rotationally symmetrically with respect to e center line 12. The cap 10 is arranged on a hollow cylinder 14 which is connected to a basic element 16. In the embodiment illustrated, the hollow cylinder 14 circular cylindrical in shape and rotationally symmetric with respect to the longitudinal axis 12.

A plunger 18 is arranged in the hollow cylinder 14 for displacement in the direction of the arrow 20. The plunger 18 is circular cylindrical and also rotationally symmetric with respect to the longitudinal axis.

In the embodiment illustrated, the cap 10 is formed integrally and comprises a female mold 22, on the upper side 24 of which in particular a plurality of preferably frusto-conical cavities is provided. This makes it possible to produce a microneedle array by filling it with a formulation. In the embodiment illustrated, the female mold 22 is surrounded by an annular reinforcing element reinforcing the edge of the female mold. The same is connected to a circular intermediate element (not shown) by which a connection to a holding element 30 is made. In the embodiment illustrated, the holding element 30 is connected to an outer side 36 of the hollow cylinder 14 using positive connecting elements 32, 34. The connecting elements are formed as, for example, an annular bead 32 provided on the outer side of the hollow cylinder 14 and cooperates with a corresponding annular recess 34 in the manner of a snap-in connection.

Since, in the embodiment illustrated, the entire cap 10 is made of a silicone material and the intermediate element has a smaller wall thickness, the intermediate element is an elongatable, in particular elastic intermediate element. A gap 48 is formed between the intermediate element and the hollow cylinder 14.

By displacing the plunger 18 upward in FIG. 1, a planar upper side 38 of the plunger comes to rest on an inner side 40 of the female mold 22. Thereby, the female mold 22 is lifted off an edge 42 of the hollow cylinder which surrounds an opening 44 of the hollow cylinder.

In an alternative embodiment, the inner side of the female mold 22 does not rest on the edge 42 of the hollow cylinder. Nevertheless, the tolerance chain is broken by lifting the female mold 22 by the plunger 18, so that only the tolerance of the thickness of the female mold 22 is relevant and the tolerances of the hollow cylinder 14 no longer have to be considered or adversely affect the quality of the microstructure to be produced.

In this lifted-off state of the female mold 22 a formulation can be applied onto the upper side of the female mold, in particular by spraying, so that the sprayed material penetrates into the cavities. Thereafter, the plunger 18 is retracted so that the inner side 40 of the female mold 22 rests on the edge 42 of the hollow cylinder 14 again and can be cured in this position.

Figure 2:
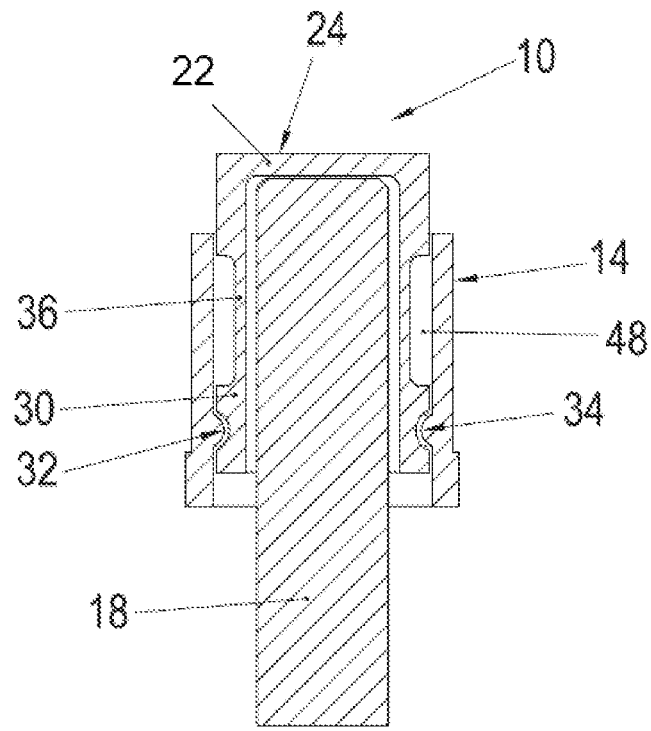
FIG. 2 shows a schematic sectional view of a second preferred embodiment of the device.

In the alternative embodiment illustrated in FIG. 2, similar or identical components are identified by the same reference numerals.

The essential difference between the two embodiments illustrated in FIGS. 1 and 2 is that the silicone cap 10 of the embodiment illustrated in FIG. 1 surrounds the hollow cylinder 14 or can be slipped onto the same, while it is arranged in the hollow cylinder 14 in FIG. 2. In this respect, in particular the holding element 30 of the cap, as well as the connecting elements 32, 34 are arranged in the hollow cylinder 14. In this embodiment, the female mold 22 does not rest on an edge of the hollow cylinder 14. For the rest, the function is identical.

Figure 3:
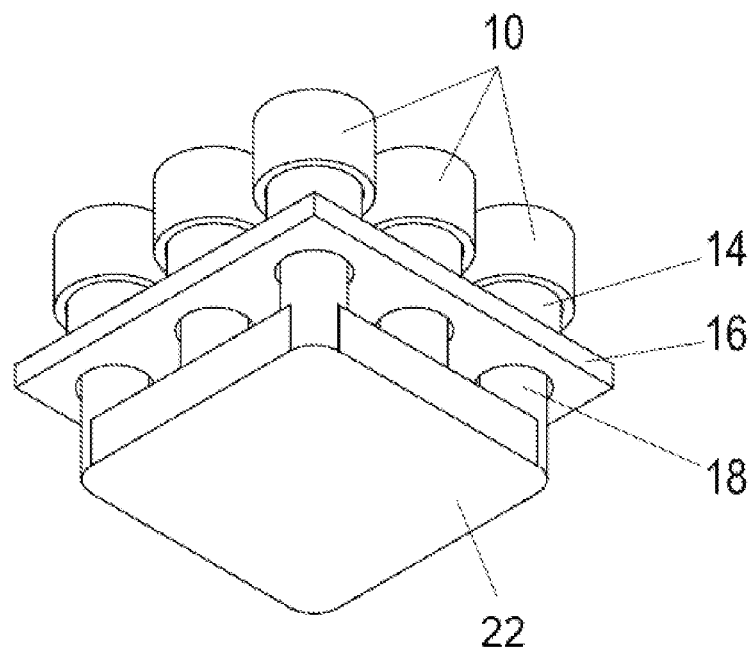
FIGS. 3 and 4 show schematic perspective views of another embodiment of the device according to the disclosure, in which a plurality of individual devices shown in FIG. 1 or 2 is combined.
Figure 4:
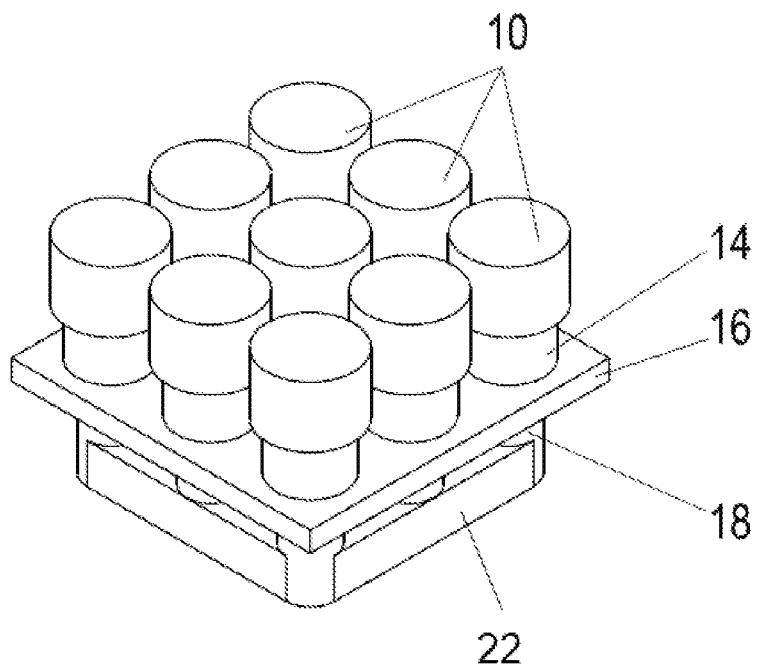

FIGS. 3 and 4 show perspective schematic views of a field or array of a plurality of devices that can be seen in FIG. 1 or 2. Here, a plurality of hollow cylinders 14 is connected via the base element 16. A corresponding number of plungers 18 in the illustrated embodiment is connected to one another via an in particular plate-shaped connecting element. Instead of the field comprising 3×3 hollow cylinders and plungers schematically illustrated in FIGS. 3 and 4, a significantly larger array of, for example, 10×10, 15×15, 20×20 hollow cylinders and plungers can be provided.

Instead of providing a field with a corresponding number of plungers 18, it is also possible to provide a group of, for example, 4, 8 or 16 plungers, so that some of the female molds are lifted by the plungers, respectively, are filled with material, and the plungers are then retracted again. Thereafter, the field of female molds and/or the group of plungers is displaced.

The invention claimed is:

1. Device for producing microstructures, comprising:
   a female mold comprising at least one preferably conical cavity at an upper side thereof for producing a microstructure, and an inner side opposite the upper side,
   a base element comprising a hollow cylinder,
   a holding element, which is connected to the female mold, for holding the female mold at the hollow cylinder such that the female mold spans an opening of the hollow cylinder, and
   a plunger arranged in the hollow cylinder and displaceable in the longitudinal direction of the hollow cylinder, wherein an upper side of the plunger rests on the inner side of the female mold.

2. Device according to claim 1, wherein the holding element comprises or is connected to a connecting element for a positive connection to the hollow cylinder.

3. Device according to claim 1, wherein the holding element surrounds the hollow cylinder.

4. Device according to claim 1, wherein the holding element rests on an inner side of the hollow cylinder completely in the circumferential direction.

5. Device according to claim 2, wherein a gap is formed between the holding element and the hollow cylinder.

6. Device according to claim 1, wherein the plunger has a planar upper side which, in an inserted position, rests on a lower side of the female mold.

7. Device according to claim 1, wherein the base element comprises a plurality of hollow cylinders.

8. Device according to claim 1, wherein a plurality of plungers is provided, which plungers are connected to one another via a connecting plate.

9. The Device according to claim 1, wherein the holding element, and the female mold are formed in one piece therewith.

10. The Device according to claim 7, wherein the plurality of hollow cylinders are connected to one another.

11. Method for producing microstructures with a device according to claim 1, the method comprising the steps of:
    inserting the at least one plunger into at least one hollow cylinder respectively, so that an upper side of the at least one plunger rests on a lower side of the female mold,
    filling the at least one cavity of the female mold with a formulation,
    retracting the plunger, and
    removing a microstructure after the curing thereof.

12. Method according to claim 11, wherein the at least one plunger is inserted such that the intermediate element is elongated and the female mold is lifted off from an edge surrounding the opening of the hollow cylinder.

13. Method according to claim 11, wherein, when the at least one plunger is retracted, the intermediate element shortens or contracts, so that the lower side of the female mold rests on the edge of the hollow cylinder surrounding the opening.

14. Method according to claim 11, wherein, if a plurality of female molds is present, these are, either individually one after the other, all together or in groups, lifted off by the at least one plunger and filled subsequently.

15. Method according to claim 11, wherein the at least one female mold is filled with a formulation via a dosing means.

* * * * *